United States Patent
Davis et al.

(10) Patent No.: US 6,241,740 B1
(45) Date of Patent: *Jun. 5, 2001

(54) SYSTEM AND METHOD OF USE FOR LIGATING AND CUTTING TISSUE

(75) Inventors: John W. Davis, Mountain View; David E. Hancock, San Francisco; Charles J. Adam, San Jose, all of CA (US)

(73) Assignee: Origin Medsystems, Inc., Menlo Park, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/058,006

(22) Filed: Apr. 9, 1998

(51) Int. Cl.[7] .................................................. A61B 17/10
(52) U.S. Cl. .............................................................. 606/139
(58) Field of Search .................................... 606/139, 142, 606/167

(56) References Cited

U.S. PATENT DOCUMENTS

| | | |
|---|---|---|
| D. 284,219 | 6/1986 | Green et al. . |
| D. 286,439 | 10/1986 | Green et al. . |
| 2,890,519 | 6/1959 | Storz, Jr. . |
| 3,006,344 | 10/1961 | Vogelfanger . |
| 3,056,408 | 10/1962 | Brown . |
| 3,175,556 | 3/1965 | Wood et al. . |
| 3,518,993 | 7/1970 | Blake . |
| 3,545,444 | 12/1970 | Green . |
| 3,579,751 | 5/1971 | Jonckheere . |
| 3,584,628 | 6/1971 | Green . |

(List continued on next page.)

FOREIGN PATENT DOCUMENTS

| | | |
|---|---|---|
| 24 21 493 | 5/1974 | (DE) . |
| 27 30 691 A1 | 7/1977 | (DE) . |
| 27 44 824 | 10/1977 | (DE) . |
| 30 44 186 A1 | 11/1980 | (DE) . |
| 0121474 | 10/1984 | (EP) . |
| 0 552 050 A2 | 7/1993 | (EP) . |
| 0 565 822 A2 | 10/1993 | (EP) . |
| 5692230A1 | 11/1993 | (EP) . |
| 406237939 | 8/1994 | (JP) . |
| WO 84/03826 | 10/1984 | (WO) . |
| WO 84/03827 | 10/1984 | (WO) . |
| WO 88/01486 | 3/1988 | (WO) . |
| WO 93/09721 | 5/1993 | (WO) . |

OTHER PUBLICATIONS

PCT International Search Report; Jun. 8, 2000.
Hulka, J.F., Laparoscopic Sterilization with the Spring Clip: Instrumentation development and current clinical experience, Am. J. Obstet. Gynecol. 135: 1016, 1979.
Abstract of Japan Patent Application No.: 6–237939.
Hulka, J.F., Laparoscopic Sterilization with Spring Clips, University of N.C. School of Medicine, 4/85.

*Primary Examiner*—Michael Buiz
*Assistant Examiner*—Anthony King
(74) *Attorney, Agent, or Firm*—Blakely, Sokoloff, Taylor & Zafman

(57) ABSTRACT

The invention is directed to a medical device for endoscopically ligating and cutting a body vessel. The device may be percutaneously inserted into a patient to perform several possible procedures. The improvements to the device include a hinged jaw capable of grasping and crimping body vessels. An improved clip delivery system and an improved clip which ligate body vessels are also described. The instrument includes a rotating cutting member which provides more efficient body vessel cutting means. Furthermore, the entire system allows a simplified and more efficient method of operation.

49 Claims, 10 Drawing Sheets

U.S. PATENT DOCUMENTS

| | | |
|---|---|---|
| 3,598,125 | 8/1971 | Cogley . |
| 3,604,425 | 9/1971 | LeRoy . |
| 3,665,924 | 5/1972 | Noiles et al. . |
| 3,675,688 | 7/1972 | Bryan et al. . |
| 3,735,762 | 5/1973 | Bryan et al. . |
| 3,740,994 | 6/1973 | DeCarlo, Jr. . |
| 3,775,825 | 12/1973 | Wood et al. . |
| 3,802,437 | 4/1974 | Kees, Jr. . |
| 3,805,792 | 4/1974 | Cogley . |
| 3,827,438 | 8/1974 | Kees, Jr. . |
| 3,882,854 | 5/1975 | Hulka et al. . |
| 3,889,683 | 6/1975 | Kapitanov et al. . |
| 3,955,581 | 5/1976 | Spasiano et al. . |
| 3,996,937 | 12/1976 | Williams . |
| 4,026,294 | 5/1977 | Mattler . |
| 4,038,987 | 8/1977 | Komiya . |
| 4,050,465 | 9/1977 | Périssé . |
| 4,064,881 | 12/1977 | Meredith . |
| 4,086,926 | 5/1978 | Green et al. . |
| 4,112,951 | 9/1978 | Hulka et al. . |
| 4,192,315 | 3/1980 | Hilzinger et al. . |
| 4,217,902 | 8/1980 | March . |
| 4,241,734 | 12/1980 | Kandel et al. . |
| 4,269,190 | 5/1981 | Behney . |
| 4,274,415 | 6/1981 | Kanamoto et al. . |
| 4,324,248 | 4/1982 | Perlin . |
| 4,340,061 | 7/1982 | Kees, Jr. et al. . |
| 4,349,028 | 9/1982 | Green . |
| 4,360,023 | 11/1982 | Sugita et al. . |
| 4,367,746 | 1/1983 | Derechinsky . |
| 4,407,285 | 10/1983 | Perlin . |
| 4,412,617 | 11/1983 | Cerwin . |
| 4,424,810 | 1/1984 | Jewusiak . |
| 4,433,689 | 2/1984 | von Zeppelin . |
| 4,434,795 | 3/1984 | Mericle . |
| 4,444,187 | 4/1984 | Perlin . |
| 4,446,865 | 5/1984 | Jewusiak . |
| 4,484,581 | 11/1984 | Martin et al. . |
| 4,492,232 | 1/1985 | Green . |
| 4,519,501 | 5/1985 | Cerwin . |
| 4,532,925 | 8/1985 | Blake, III . |
| 4,548,201 | 10/1985 | Yoon . |
| 4,556,058 | 12/1985 | Green . |
| 4,569,346 | 2/1986 | Poirer . |
| 4,576,165 | 3/1986 | Green et al. . |
| 4,576,166 | 3/1986 | Montgomery et al. . |
| 4,602,629 | 7/1986 | Schnirman . |
| 4,602,631 | 7/1986 | Funatsu . |
| 4,602,632 | 7/1986 | Jorgensen . |
| 4,616,651 | 10/1986 | Golden . |
| 4,637,395 | 1/1987 | Caspar et al. . |
| 4,658,822 | 4/1987 | Kees, Jr. . |
| 4,660,558 | 4/1987 | Kees, Jr. . |
| 4,662,373 | 5/1987 | Montgomery et al. . |
| 4,662,374 | 5/1987 | Blake, III . |
| 4,665,916 | 5/1987 | Green . |
| 4,671,278 | 6/1987 | Chin . |
| 4,681,109 | 7/1987 | Arroyo . |
| 4,682,598 | 7/1987 | Beraha . |
| 4,686,983 | 8/1987 | Leisman et al. . |
| 4,706,668 | 11/1987 | Backer . |
| 4,716,886 | 1/1988 | Schulman et al. . |
| 4,765,335 | 8/1988 | Schmidt et al. . |
| 4,777,949 | 10/1988 | Perlin . |
| 4,777,950 | 10/1988 | Kees, Jr. . |
| 4,788,966 | 12/1988 | Yoon . |
| 4,791,707 | 12/1988 | Tucker . |
| 4,796,625 | 1/1989 | Kees, Jr. . |
| 4,796,627 | 1/1989 | Tucker . |
| 4,799,481 | 1/1989 | Transue et al. . |
| 4,805,618 | 2/1989 | Ueda et al. . |
| 4,821,721 | 4/1989 | Chin et al. . |
| 4,834,096 | 5/1989 | Oh et al. . |
| 4,850,355 | 7/1989 | Brooks et al. . |
| 4,854,317 | 8/1989 | Braun . |
| 4,869,268 | 9/1989 | Yoon . |
| 4,877,028 | 10/1989 | Sandhaus . |
| 4,924,864 | 5/1990 | Danzig . |
| 4,929,239 | 5/1990 | Braun . |
| 4,932,955 | 6/1990 | Merz et al. . |
| 4,935,026 | 6/1990 | McFadden . |
| 4,943,298 | 7/1990 | Fujita et al. . |
| 4,957,500 | 9/1990 | Liang et al. . |
| 4,961,743 | 10/1990 | Kees, Jr. et al. . |
| 4,966,603 | 10/1990 | Focelle et al. . |
| 4,976,722 | 12/1990 | Failla . |
| 4,979,950 | 12/1990 | Transue et al. . |
| 4,983,176 | 1/1991 | Cushman et al. . |
| 5,026,379 | 6/1991 | Yoon . |
| 5,026,382 | 6/1991 | Peiffer . |
| 5,035,692 | 7/1991 | Lyon et al. . |
| 5,053,045 | 10/1991 | Schmidt et al. . |
| 5,059,202 | 10/1991 | Liang et al. . |
| 5,071,430 | 12/1991 | de Salis et al. . |
| 5,074,870 | 12/1991 | von Zeppelin . |
| 5,078,731 | 1/1992 | Hayhurst . |
| 5,100,416 | 3/1992 | Oh et al. . |
| 5,100,420 | 3/1992 | Green et al. . |
| 5,104,394 | 4/1992 | Knoepfler . |
| 5,171,250 | 12/1992 | Yoon . |
| 5,190,560 | 3/1993 | Woods et al. . |
| 5,205,459 | 4/1993 | Brinkerhoff et al. . |
| 5,207,691 | 5/1993 | Nardella . |
| 5,207,692 | 5/1993 | Kraus et al. . |
| 5,217,030 | 6/1993 | Yoon . |
| 5,217,473 | 6/1993 | Yoon . |
| 5,226,908 | 7/1993 | Yoon . |
| 5,242,456 | 9/1993 | Nash et al. . |
| 5,258,007 | 11/1993 | Spetzler et al. . |
| 5,271,544 | 12/1993 | Fox et al. . |
| 5,275,322 | 1/1994 | Brinkerhoff et al. . |
| 5,282,811 | 2/1994 | Booker et al. . |
| 5,285,945 | 2/1994 | Brinkerhoff et al. . |
| 5,292,053 | 3/1994 | Bilotti et al. . |
| 5,304,183 | 4/1994 | Gourlay et al. . |
| 5,306,280 | 4/1994 | Bregen et al. . |
| 5,306,283 | 4/1994 | Conners . |
| 5,312,426 | 5/1994 | Segawa et al. . |
| 5,334,209 | 8/1994 | Yoon . |
| 5,340,360 | 8/1994 | Stefanchik . |
| 5,342,373 | 8/1994 | Stefanchik et al. . |
| 5,354,304 | 10/1994 | Allen et al. . |
| 5,366,458 | 11/1994 | Korthoff et al. . |
| 5,368,600 | 11/1994 | Failla et al. . |
| 5,395,381 | 3/1995 | Green et al. . |
| 5,431,668 | 7/1995 | Burbank, III et al. . |
| 5,447,513 | 9/1995 | Davison et al. . |
| 5,454,826 | 10/1995 | Ueda . |
| 5,464,416 | 11/1995 | Steckl . |
| 5,474,567 | 12/1995 | Stefanchik et al. . |
| 5,478,353 | 12/1995 | Yoon . |
| 5,480,640 | 1/1996 | Morales et al. . |
| 5,486,185 | 1/1996 | Freitas et al. . |
| 5,501,693 | 3/1996 | Gravener . |
| 5,518,164 | 5/1996 | Hooven . |
| 5,527,319 | 6/1996 | Green et al. . |
| 5,554,164 | 9/1996 | Wilson et al. . |
| 5,569,274 | 10/1996 | Rapacki et al. . |
| 5,571,120 | 11/1996 | Yoon . |
| 5,571,121 | 11/1996 | Heifetz . |
| 5,593,414 | 1/1997 | Shipp et al. . |

| | | | | | |
|---|---|---|---|---|---|
| 5,601,573 | 2/1997 | Fogelberg et al. . | 5,766,189 | 6/1998 | Matsuno . |
| 5,695,505 | 12/1997 | Yoon . | 5,810,847 | 9/1998 | Laufer et al. . |
| 5,704,943 * | 1/1998 | Yoon et al. ............... 606/139 | 5,810,882 | 9/1998 | Bolduc et al. . |
| 5,725,542 | 3/1998 | Yoon . | 5,911,728 | 6/1999 | Sepetka et al. . |
| 5,733,295 | 3/1998 | Back et al. . | | | |
| 5,752,964 | 5/1998 | Mericle . | | | |

* cited by examiner

SYSTEM AND METHOD OF USE FOR LIGATING AND CUTTING TISSUE

BACKGROUND OF THE INVENTION

This invention generally relates to devices for performing endoscopic medical procedures. More specifically, this invention relates to devices for ligating and cutting body vessels. When performing medical procedures it is often necessary to ligate, or block the flow of, by crimping, a body vessel such as a vein or artery. It may also be necessary to cut the vessel. In endoscopic procedures the surgical treatment occurs at a distance, through a small incision in the patient's skin. In these procedures cutting and ligating vessels generally requires specialized instrumentation inserted through the incision. Even with such instrumentation these functions can be challenging.

When grasping a vessel in preparation of other procedures it is important to obtain a secure grip on the vessel. It is also important to avoid dislodging the vessel from its normal position. Vessels which are not securely grasped are difficult to ligate and cut. Vessels which are dislodged from their normal position may spring back or recede from their new position once the procedure has been completed. Additionally, vessels which are dislodged may avulse, or damage connecting main branches, or in other words, moving a tributary may damage a saphenous vein. Loosely grasped vessels unduly complicate the medical procedure. Furthermore, after cutting a vessel in two or more places, a securely grasped vessel can be "harvested" by withdrawing the instrument and the grasped vessel.

Many current devices grasp body vessels by sliding over them in an effort to trap them within the instrument. This procedure produces an insecurely grasped vessel, due to the one-way trapping employed. This procedure also presents an uncertainty as to whether the vessel is adequately trapped within the instrument. Furthermore, these devices tend to dislodge the vessel from its normal position in an effort to trap the vessel. This is especially so for minimally invasive devices which are often very long. The normal movement of the operators hands is multiplied by the length of the device, so distal tip manipulation is difficult to control.

When ligating a vessel it is important to completely and securely cut off the flow of the vessel. The clips used for ligation need to maintain a sufficient compression on the vessel to stop flow within the vessel and to remain secured on the vessel. Clips which leak or become dislodged from the vessel unduly complicate the medical procedure.

Current devices use several different methods of ligating a body vessel. One method uses a closed clip construction of a particular configuration, which requires the clip to be mechanically bent open by an applicator to advance the clip over the body vessel. This requires the clip to be flexible enough so that bending the clip open will not permanently deform the clip more than is necessary to apply the clip. A more flexible clip will most likely be larger in size or have lower retention force to the vessel it is applied to.

Another method uses an open clip construction, which requires the clip to be crimped after advancing the clip over the body vessel. This requires the medical device to provide sufficient force to permanently deform the clip over the body vessel. As in the first method, this requires the clip to be formed of relatively flexible material. Regardless of the material used, the permanent deformation during crimping can compromise compression strength by reducing the spring forces in the clip. Open clips take up more space and thus require larger delivery systems. Creating the great force necessary to close clips tends to be quite complex when it must be done in a small, disposable delivery system. Closed clips require much less force to apply, are easier to apply (because the force is applied along the length of the device and not perpendicular to it), and have tighter dimensional control in their applied state because they are closed in a manufacturing environment with clip forming machinery.

When cutting body vessels it is important to maintain a consistent cutting force so that the cut edges of the vessel are even and consistent. Inconsistent or uneven edges may be difficult to later re-attach or permanently close. Current devices use a scissoring method with a hinged lever-type action to cut a vessel. Such a method produces a cutting force which varies with the distance from the hinge point. Variations in cutting force varies the cutting efficiency and may produce uneven edges or an incomplete cut.

Since many different procedures exist which require endoscopic ligating and cutting of vessels it is necessary that the device be capable of variable and multiple functions within a single procedure. Such operating flexibility has been difficult to achieve in a simple, easy to use device. The complexity of endoscopic surgery requires that the instrumentation be easily manageable. A simple hand-held device with a minimum of control mechanisms is preferrable to more complex designs.

One of the great difficulties associated with minimally invasive surgery is the time required to change out the surgical tools. Minimally invasive surgery is typically performed through a small number of "ports" that are often not near to the targeted surgical region. This limits the number of devices allowable and hinders the locating of the business ends of the devices at the surgical region. Multi-function devices help in this regard.

What has been needed and heretofore unavailable is an endoscopic instrument which is capable of efficiently ligating and cutting a body vessel and having sufficient operating flexibility to be used in various procedures. Furthermore, a ligating clip has been needed which completely and reliably stops the flow through a body vessel during surgery. The present invention satisfies these needs.

SUMMARY OF THE INVENTION

The invention is directed to novel features in a medical device for cutting and ligating body vessels. The improvements include a hinged jaw to grasp the vessel, an improved delivery system of an improved ligating clip and a rotating cutter. The hinged jaw improves the efficiency of grasping the body vessel by not sliding over the vessel during insertion of the instrument, and then clamping down securely over the vessel. An improved ligating clip is provided which does not lose compression strength due to overbending during the procedure. The ligating clip delivery system is configured to store and deploy the improved clips without bending or crimping during the procedure. The rotating cutter is able to provide a more efficient cut by avoiding the deficiencies of previous cutters. The co-location of these features provides user flexibility and eliminates the time usually spent on changing out single function tools.

The instrument's distal end, containing manipulating devices, is percutaneously inserted into a patient, so that an operator can manually control the procedure by using the instrument's control devices located outside the patient. The instrument's manipulating devices can then be advanced over selected body vessels. The instrument, controlled by the operator, then grasps the vessel using a hinged jaw. Once the vessel is grasped, the operator, using the control devices, proceeds to ligate or cut the body vessel. The operator may perform either or both of these functions in any order desired.

This instrument provides improved ligating of body vessels. Because the instrument advances the clip over the vessel, rather than bending the clip open and then releasing the clip over the vessel, the clip can be composed of very stiff material without compromising the compression force due to over bending. Both the instrument and the clip of the present invention include improvements which allow the clip simply to be advanced over the vessel. This allows for smaller clips (open clips take more space), which, in turn, allows for a smaller instrument, which allows for a smaller percutaneous incision.

This instrument also provides improved cutting of body vessels. By using a rotating cutter this invention avoids the variation in cutting force typical of other cutters. This consistency in cutting force leads to cleaner and more efficient cuts. Moreover, equipping the instrument with bi-directional cutting capabilities, versatility as well as the cutting function itself are enhanced. Additionally, co-location of the cutter and ligator minimizes the amount of vessel tissue extending beyond the clip application site, which, in turn, thereby maximizes the length of a vessel being harvested and eliminates the chance of inadvertently cutting non-target tissue.

Other features and advantages of the invention will become apparent from the following detailed description, taken in conjunction with the accompanying drawings, which illustrate, by way of example, the features of the invention.

DETAILED DESCRIPTION OF THE PREFERRED EMBODIMENTS

Figure 1:
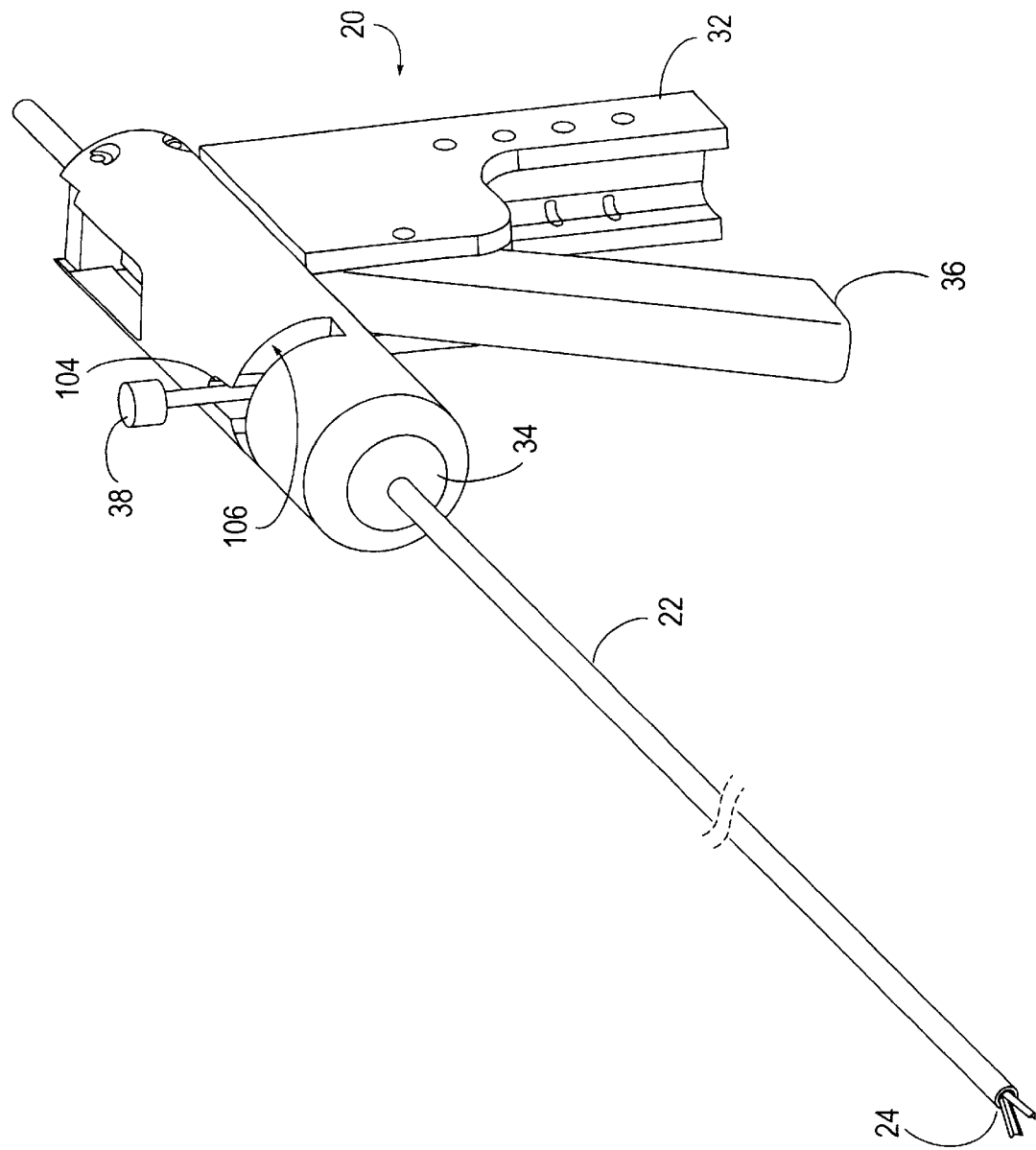
FIG. 1 is a perspective view depicting a medical instrument embodying the features of the invention.

FIGS. 1 through 4 illustrate a medical instrument 10 embodying the features of this invention, which is designed to grasp, ligate, and possibly cut a body vessel. Generally the invention includes an actuating assembly 20 at one end, an elongated shaft 22 extending distally away from the actuating assembly, and a manipulating assembly 24 at the distal end of the shaft. The actuating assembly is handled by the operator and includes the devices which control the operation of the instrument. The distal end of the instrument, including the manipulating assembly and portions of the elongated shaft, can be percutaneously inserted into a patient. The manipulating assembly can then be positioned onto the body vessel being treated. The manipulating assembly can then be used to grasp, ligate, and possibly cut the body vessel.

Similar instruments, known in the art, are used to grasp, ligate and cut body vessels. These devices often use grasping means which require sliding the instrument over the vessel in order to trap the vessel. The devices ligate the vessel either by mechanically bending open a closed clip and then advancing the clip over the vessel and releasing the clip, or advancing an open clip over the vessel and crimping the clip onto the vessel. The cutting means of these devices use either lever-type scissors or a razor to cut the vessel. The improvements of the present invention include, grasping the vessel within the instrument's jaw 26, advancing an improved clip 28 over the vessel without bending or crimping the clip, and a rotating cutting means.

Figure 5:
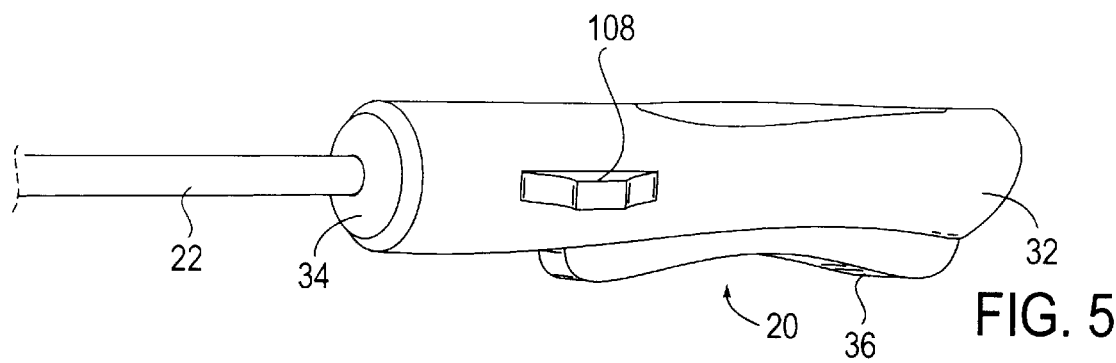
FIG. 5 is a perspective view of an alternative preferred embodiment of the applicator.

This invention, as with similar instruments, is designed to be operated manually. Therefore, the actuating assembly 20 is equipped with a handle 32 which can be used by the operator to position the instrument within a patient's body. The handle is attached to a barrel 34 which is disposed generally perpendicular to the handle, but can also be parallel or in line with the barrel (See FIG. 5). The actuating assembly is also equipped with at least one trigger 36 and at least one cutting knob, button or lever 38 which are adapted for manual operation of the devices at the distal tip of the elongated shaft 22. The elongated shaft and manipulating assembly 24 are sufficiently narrow, approximately 5 mm, to be percutaneously inserted into the patient and advanced through the body to a body vessel to be treated. Once the manipulating assembly is properly positioned over a body vessel this invention is capable of multiple procedures.

Figure 2:
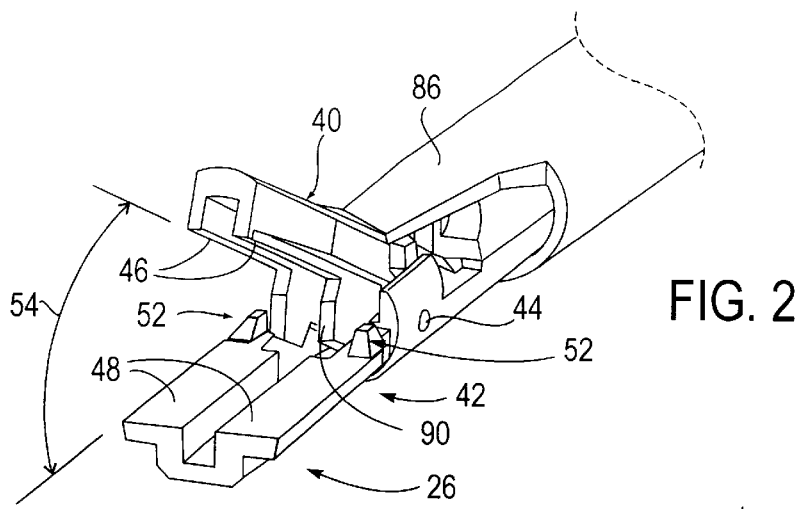
FIG. 2 is a perspective view of the distal end of the medical instrument of FIG. 1 depicting the manipulating assembly with the jaw in the open position.
Figure 3:
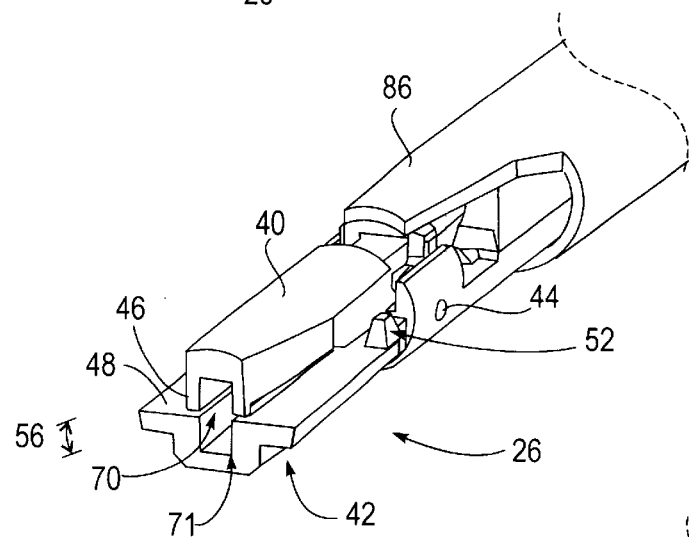
FIG. 3 is a perspective view depicting the manipulating assembly of FIG. 2 with the jaw in the closed position.
Figure 6:
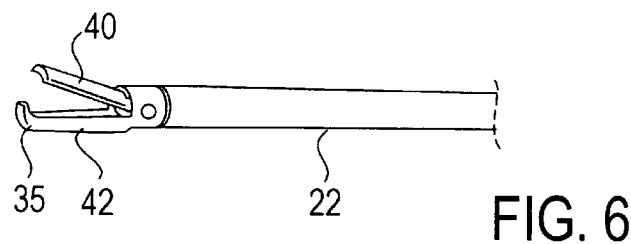
FIG. 6 is a perspective view of one embodiment of the manipulating assembly, illustrating a hook for a acquiring vessels.

FIGS. 2 and 3 illustrate the grasping procedure of the invention which is accomplished using the jaw 26. The figures illustrate, by way of example, the jaw having a hinged jaw member 40 and a fixed jaw member 42 both extending away from the distal tip of the shaft. The hinged jaw member is attached to a hinge 44 near the attachment between the fixed jaw member and the distal tip of the elongated shaft 22. The hinged jaw member has a grasping surface, 46 and the fixed jaw member has a grasping surface 48. These surfaces are designed to receive a body vessel and hold it securely. In a preferred embodiment at least one of the grasping surfaces includes a stop or arm 90 near the proximal end of the surface to aid in preventing the vessel being inserted too far into the device. The upper jaw member and the lower jaw member may also define a channel 70 between them. The channel defines an opening 71 at the distal end of the jaw and continues proximally through the jaw. Grasping surfaces 46, 48 can have geometry (eg. teeth)or surface treatments (eg., sticky coating) for facilitating grasping. Moreover, either jaw may have a distal hook 35 to aid in acquiring the vessel (See FIG. 6).

The configuration depicted defines two positions for the jaw. In the open position 54 the grasping surfaces 46, 48 of the hinged jaw member 40 and the fixed jaw member 42 are spread apart. In this open position the jaw may be advanced over a body vessel 50. In the closed position 56 the grasping surface of the hinged jaw member 46 and the grasping surface of the fixed jaw member 48 are in contact or in close proximity with each other. In this position, the jaw 26 firmly grasps the body vessel.

Figure 7:
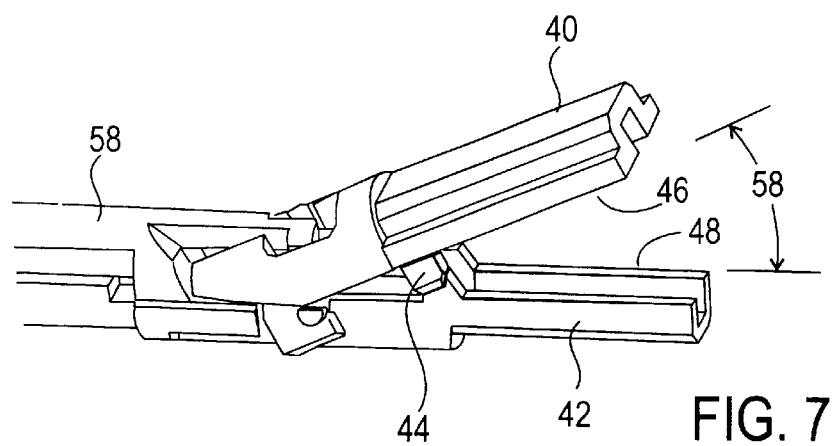
FIG. 7 is a partial cross-sectional side view depicting the manipulating assembly of FIG. 2 with the jaw in the open position.
Figure 8:
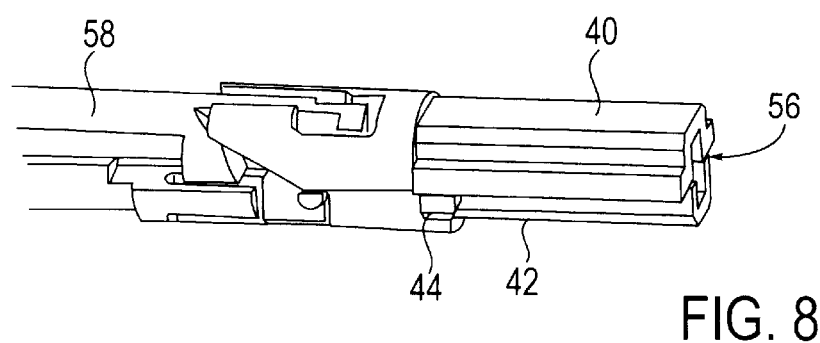
FIG. 8 is a partial cross-sectional side view of the manipulating assembly of FIG. 3 with the jaw in the closed position.
Figure 9:
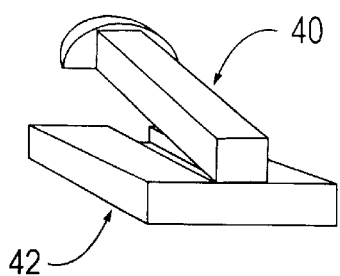
FIG. 9 is a perspective view of one embodiment of the manipulating assembly, illustrating flares positioned on the manipulating assembly.
Figure 10:
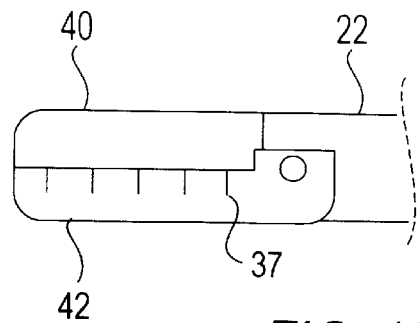
FIG. 10 is a side view of one embodiment of the manipulating assembly, illustrating depth indicators configured on the manipulating assembly.

In the embodiment illustrated, the hinged jaw member 40 extends proximally beyond the hinge 44 (See FIGS. 7 and 8). Either jaw member may have flares or depth indicators 37 to assist the visualization of the vessel within the jaws (See FIGS. 9 and 10). The pushrod 58 is spring loaded so that the hinged jaw member can be in the open or closed position 54 or 56. When a first pushrod 58 is advanced forward into the proximal end of the hinged member it actuates the hinge member into the closed position 56 (See FIGS. 7 and 8). When a first pushrod 58 is advanced backward away from the hinged member it actuates the hinge member into the open position 54. The first pushrod is housed within or can be part of the elongated shaft 22 and extends proximally through the shaft to the actuating assembly 20. At the actuating assembly the first pushrod is connected to the trigger 36 so that squeezing the trigger advances the first pushrod and actuates the jaw into the closed position. The trigger, or first pushrod, can be spring loaded so that releasing the trigger retracts the first pushrod and actuates the jaw into the open position.

Figure 11:
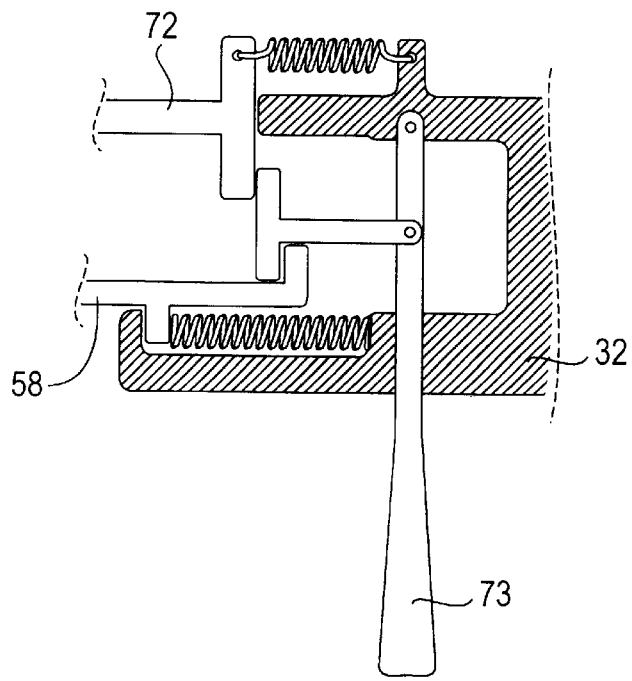
FIG. 11 is a partial cross-sectional view of the actuation assembly of yet another preferred embodiment.

In one preferred embodiment of the actuation assembly (See FIG. 11), the trigger and jaws are in the reverse configuration where jaws are spring loaded to the closed position and squeezing the trigger will open the jaws. When the trigger is released the jaws are pushed back to the closed position by the spring force. This allows the user the ability to not have to hold the jaws closed while a clip is being applied or the vessel is being cut.

Figure 12:
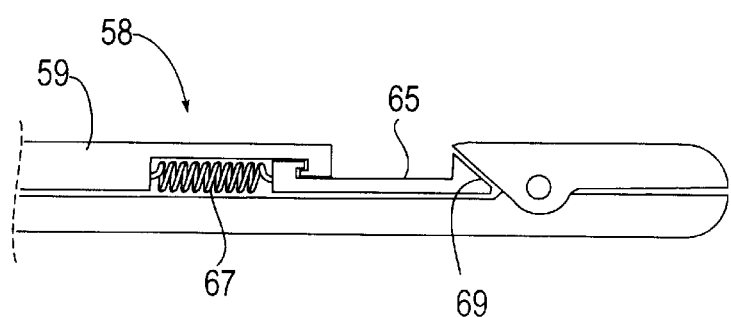
FIG. 12 is a side view of an alternative preferred embodiment of a pushrod assembly.

As shown in FIG. 12, in one preferred embodiment, the first pushrod 58 is an assembly embodying a proximal portion 59, a distal portion 65 and a spring 67 interspaced therebetween. The distal portion includes an angled surface 69 which engages that part of the jaw member which extends proximally beyond the hinge 44, and by way of a wedging action, operates to close the jaws. By so configuring the assembly with spring 67, the jaws can be closed with the specified force supplied by the spring. This limits the closing force so tissue inside the jaws does not get squeezed to the point of being damaged. Further, the wedging action makes it more difficult for the jaws to be pried open at the mouth thereof by a spring clip that is being applied to a vessel that is bunching up or expanding in some manner within the jaws.

This invention will also be operable with embodiments not illustrated in the figures. The jaw may be composed of two hinged members which operate in unison or otherwise. The hinged members may be actuated by similar mechanical or assisted mechanical means such as electric, hydraulic or pneumatic means. Instead of a trigger, the control device may be configured as a button, a switch or any equivalent device.

This invention is contemplated to ligate the body vessel using an improved clip 28. The clip can be configured in several ways as illustrated by FIGS. 13 through 21. Essentially the clip is a single component folded or twisted onto itself so that an upper member 60 and a lower member 62 are formed. A compressive force is provided at the distal end between these members as they are compressed together ie. folded over on each other. This configuration also defines a receiving end 63 of the clip and a closed end 61 of the clip.

The improvement of this clip is that during ligation the members 60, 62 only open as wide as necessary to enclose the body vessel 50 to be treated. The members have lips 64 formed at the receiving end 63 of the clip by diverging the upper member 60 and lower member 62 away from each other at their ends. These lips allow the clip to receive the vessel between the upper member and lower member and spread the members apart as the vessel passes through the clip. This improvement allows the clip to be spread over the vessel with a minimum of bending. Also the compressive (spring load) forces between the members will never be less than their maximum potential because the members will never be bent open more than is necessary to receive the vessel. While stiffer materials provide greater compressive forces, they are also more likely to permanently deform if the clip is bent open by the instrument for the purpose of receiving a vessel. Therefore, with this improvement the clip can be composed of as stiff a material as possible without compromising the compressive forces due to overbending.

Figure 13:
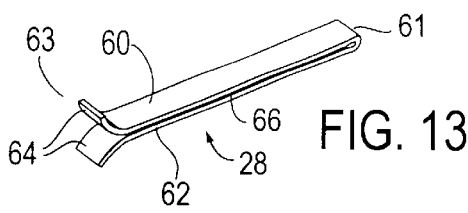
FIG. 13 is an enlarged perspective view depicting a first embodiment of a ligating clip.

In a preferred embodiment, as shown in FIG. 13, the clip 28 is formed from a narrow thin plate, flat wire or even square wire which is folded onto itself leaving a compressive force between its two members 60 and 62. The lips 64 are formed by bending the tips of the plate away from each other at the receiving end 63. Vessel retention structure may be configured on opposed faces which separate to increase stability of the clip on the vessel. In its relaxed state, the retention surfaces may be in contact under force or there may be a slight gap therebetween.

Figure 14:
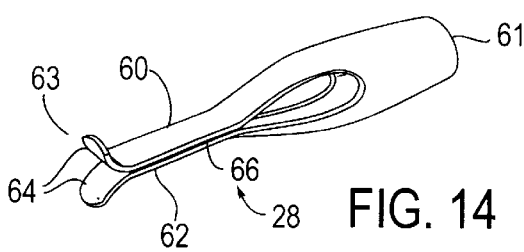
FIG. 14 is an enlarged perspective view depicting a second embodiment of a ligating clip.

In one embodiment, shown in FIG. 14, the clip 28 is formed as a closed tubular member at the closed end 61 and narrows to two flat plates at the receiving end 63. The lips 64 are formed by bending the plates away from each other at their tips.

Figure 15:
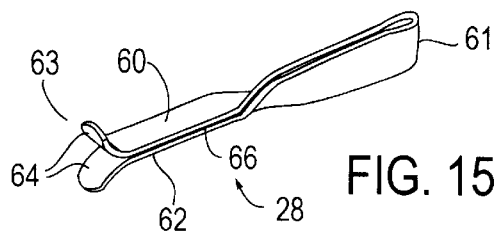
FIG. 15 is an enlarged perspective view depicting a third embodiment of a ligating clip.

In another embodiment, shown in FIG. 15, the clip 28 is formed from a flat plate which is folded onto itself and then twisted. The twist adds reinforcement to the moment that supplies the compressive force between the distal ends of the members 60 and 62. The lips 64 are formed by bending the tips of the plate away from each other at the receiving end 63.

Figure 16:
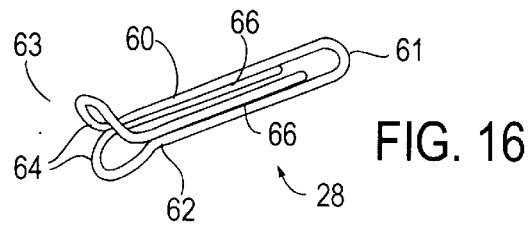
FIG. 16 is an enlarged perspective view depicting a fourth embodiment of a ligating clip.
Figure 21:
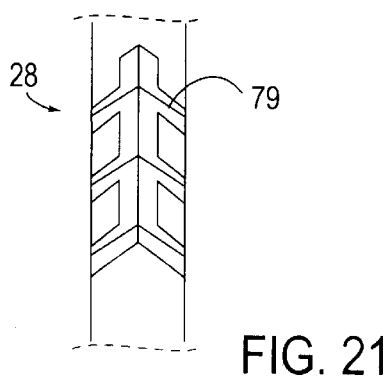
FIG. 21 is an enlarged partial view of a ligating clip, depicting the ligating surfaces thereof.

In a further embodiment, shown in FIG. 16, the clip 28 is formed from a single wire twisted to form two ligating surfaces 66 similar to a paper clip with the bonding surfaces in the same horizontal plane. The mouth 64 is formed by bending the wire segments away from each other at the receiving end 63.

Figure 17:
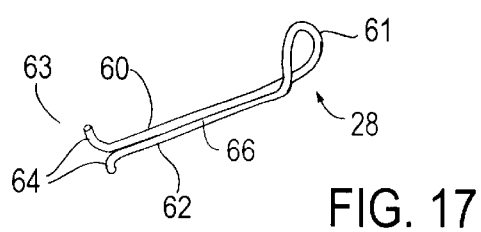
FIG. 17 is an enlarged perspective view depicting a fifth embodiment of a ligating clip.

In yet another embodiment, shown in FIG. 17, the clip 28 is formed from a single wire folded onto itself to form the single ligating surface 66. The lips 64 are formed by bending the wire ends away from each other at the receiving end 63. The wire is twisted near the closed end to help prevent the body vessel 50 from advancing too far into the clip.

Figure 18:
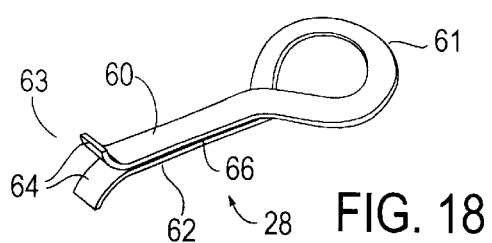
FIG. 18 is an enlarged perspective view depicting a sixth embodiment of a ligating clip.

In another alternative embodiment, shown in FIG. 18 the clip 28 is formed from a narrow thin plate which is twisted onto itself forming a loop at the closed end 61. The lips 64 are formed by bending the tips of the plate away from each other at the receiving end 63.

Figure 19:
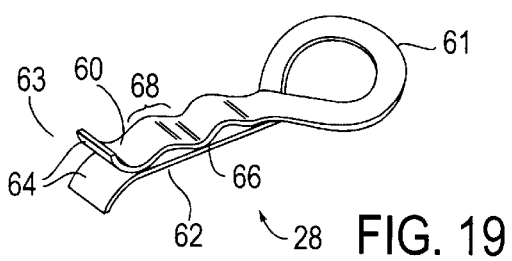
FIG. 19 is an enlarged perspective view depicting an seventh embodiment of a ligating clip.

A modification which can be applied to all of the configurations is illustrated in FIG. 19. By forming waves 68 in one or both of the members 60 and 62, the clip 28 will form alternating areas of relatively high and relatively low compression at the ligating surface 66. The relatively high areas of compression will increase the grasping force on the body vessel 50.

Figure 20:
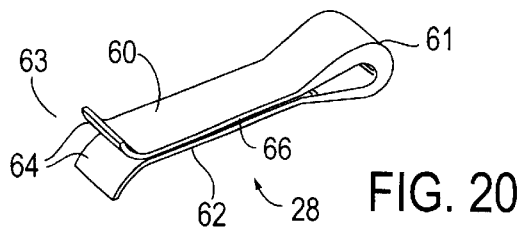
FIG. 20 is an enlarged perspective view depicting a eighth embodiment of a ligating clip.

FIG. 20 illustrates a modification which can be applied to all of the configurations. By increasing the radius of curvature of the bends in the clip 28 near the closed end 61 a stiffer material can be used so the clip will have a higher spring force, creating a higher compression force at the ligating surface 66, while allowing a sufficient flexibility near the receiving end 63.

Another modification, not illustrated, is to have a small gap between the members 60, 62 as opposed to having them in contact when the clip 28 is closed. This modification permits larger vessels to be ligated without overbending the clip. The gap may also become narrower or wider toward the closed end 61 of the clip.

The ligating surfaces 66 of the clip members 60, 62 may also be modified to minimize slip across the surface. The surface may be notched, knurled, scaled or filed. Many patterns can be made into the bonding surfaces. (See for example FIG. 21, which illustrates a surface embodying oriented chevron shaped recesses 79.)

The ligating surfaces 66 of the clip may be modified with various means to further prevent slippage. Mechanical means such as interlocking teeth either lengthwise or cross wise may be employed. The clips may also include a shark tooth configuration, wherein the surface contains sharp ridges with edges facing the closed end 61 of the clip. The surfaces may also be coated with non-slip substances, such as silicone rubber.

When the jaw 26 has grasped a body vessel 50 the instrument is in position to ligate the vessel. The jaw also crimps the vessel into a low profile which facilitates the application of the clip 28. The clip is advanced out of a channel 70 defined in the jaw and over the crimped body vessel.

Figure 22:
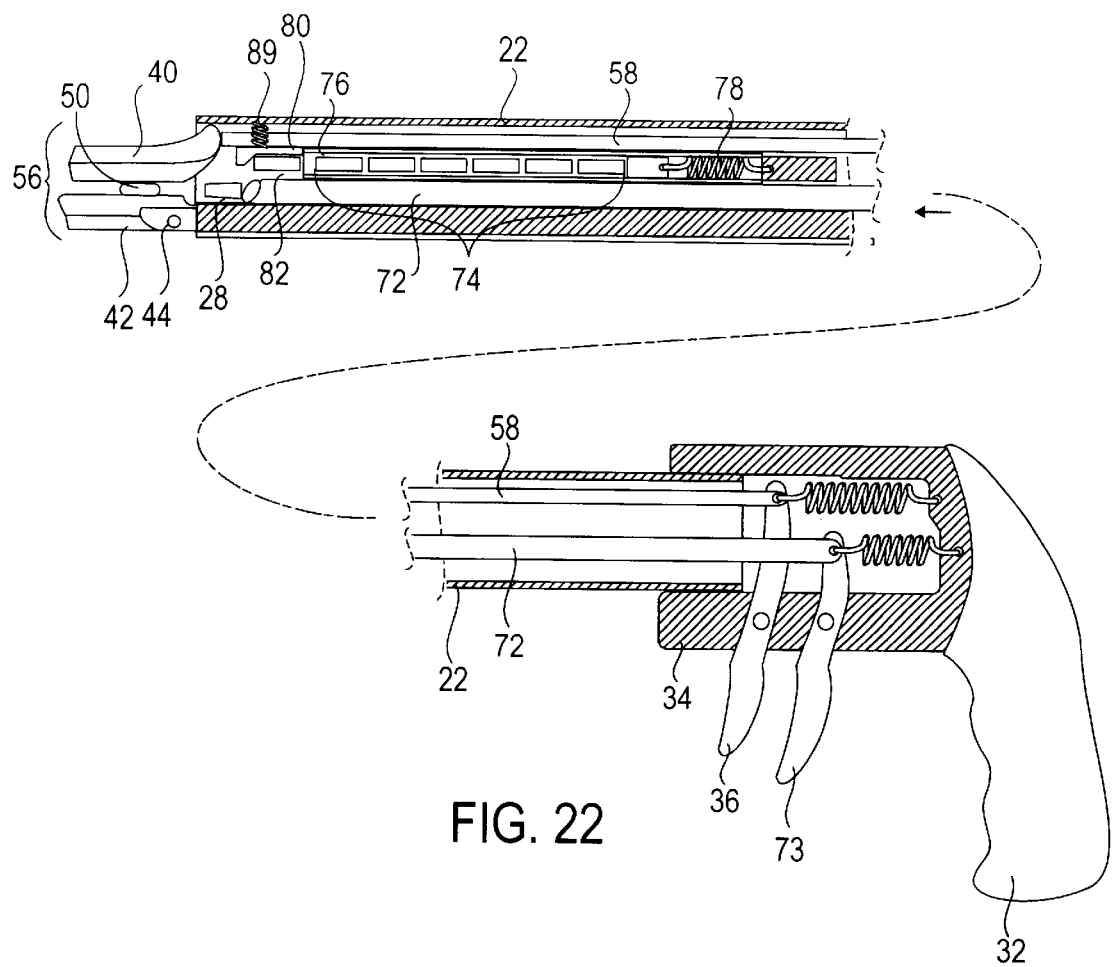
FIG. 22 is a cross-sectional side view depicting the clip storage and loading features of the invention.

FIG. 22 illustrates, by the way of example, the ligating function of the invention. A clip 28 is disposed within the elongated shaft 22 adjacent the jaw 26. A second pushrod 72, in-line with the clip, is used to distally advance the clip through the channel 70 defined in the fixed jaw member 42 and the hinged jaw member 40. The channel is configured so that it is in-line with, and accessible by, the second pushrod and the clip only when the jaw is in the closed position 56. Furthermore, the crimped body vessel is positioned by the jaw to be in-line with the receiving end 63 of the clip. Therefore, advancing the second pushrod advances the clip over the body vessel which spreads the members 60, 62 of the clip until the body vessel is fully ligated.

Figure 23:
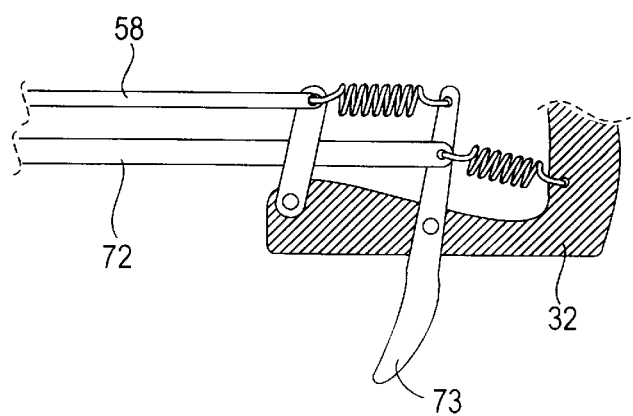
FIG. 23 is a partial cross-sectional view depicting the trigger mechanism of another preferred embodiment.

The second pushrod 72 is housed within the elongated shaft 22 and extends proximally through the shaft. At the actuating assembly 20, the second pushrod is attached to a second trigger 73 so that squeezing the second trigger advances the second pushrod and advances the clip over the body vessel 50. The second trigger and/or the second pushrod are spring loaded so that the second pushrod is retracted when the second trigger is released. In another preferred embodiment FIG. 23, the first pushrod 58 and second pushrod 72 are coupled together to one trigger 73 which both actuates the jaw and advances the clip. The assembly of the pushrods and trigger may be configured so that different positions of the trigger may define different functions being performed by the pushrods. This invention is also operable with embodiments not illustrated in the figures. The clip advancing function of the medical device has been described as a simple mechanical device. Many more complex devices are able to perform this function as well. An electric device may advance the clips and pushrod using an electric motor. Pneumatic or hydraulic means may be utilized by forcing a fluid behind the pushrod so that it extends like a piston. Furthermore, other mechanical means may be employed to advance the clips over the vessel.

This instrument may be configured to house and deploy several clips within a single procedure. FIG. 22 illustrates, by way of example, the features associated with this improvement. A plurality of clips 74 may be housed within a separate storage tube 76. The storage tube may be of any configuration which facilitates the storage of multiple clips while allowing for the deployment of clips as they are to be used. As an example, the storage tube may be a tubular shaft, slightly larger in diameter than the clips, extending through the elongated shaft 22. The proximal end of the storage tube contains an advancing spring 78 which acts to force the plurality of clips distally. At the open distal end of the storage tube, a side ram 80 defines a staging area 82. The staging area may be configured to accept a single clip advancing distally from the storage tube due to the force of the advancing spring. The side ram includes a loading spring 84 which acts to force the side ram, and the clip in the staging area, into position to be advanced by the second push rod 72.

When the second pushrod 72 is in a distally advanced position, it prevents the loading of the clip 28 in the staging area 82 by occupying the area to which the clip would be loaded. When the second pushrod is retracted, the distal end of second pushrod is proximal to the staging area and side ram 80. This allows the loading spring 84 to force the side ram, staging area, and clip to a position in-line and distal to the second pushrod. As the second pushrod is advanced distally with the side ram, staging area, and clip in-line with the second push rod, the side ram is configured to be forced back in-line with the storage tube 76, compressing the loading spring 84. Furthermore, the side ram is configured so that as it is forced back in-line with the storage tube, the clip 26 in the staging area is left in-line with the second pushrod. This leaves the staging area empty so that another clip is advanced into it as it returns to a position in-line with the storage tube. The clip that is in-line with the second pushrod is now ready to be advanced through the channel 70 and over the vessel 50.

Figure 24:
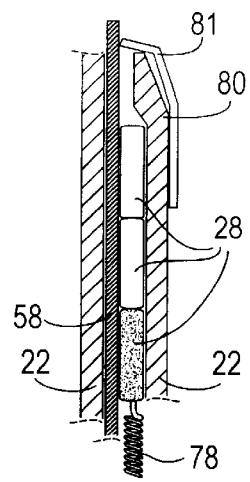
FIG. 24 is a partial cross-sectional view of the feed mechanism of another preferred embodiment.
Figure 25:
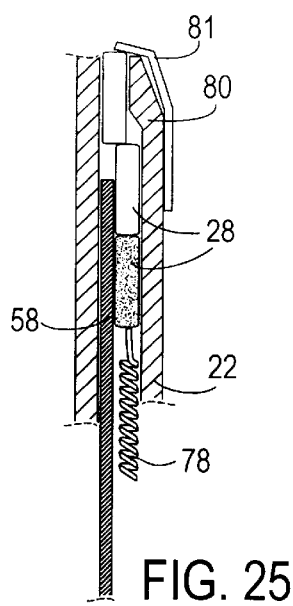
FIG. 25 is a partial cross-sectional view of the feed mechanism shown in FIG. 24, with the first pushrod moved proximally.
Figure 26:
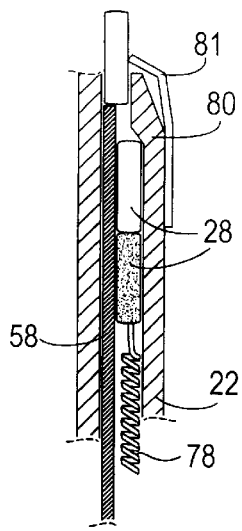
FIG. 26 is a partial cross-sectional view of the feed mechanism shown in FIG. 25, with the first pushrod moved distally.

The embodiments of these features may vary without affecting the operability of the invention. The staging and loading of the clips may be accomplished with similar mechanical and mechanical assisted means. As shown in FIGS. 24–26, for example, the feed mechanism can include a leaf spring 81 which cooperates with side ram 80 to accomplish loading a clip 28 for application upon a vessel. In this embodiment, when the first pushrod 58 is pulled proximately, the lead clip is pushed forward by the force applied by advancing spring 78 and is guided sideways by sideram 80 into a position beyond and in line with the first pushrod 58. The longitudinal movement of the pushrod 58 is such that its distal end travels a distance great enough to make room for a single clip 28 in the staging area. The leaf spring 81 is stiff enough to maintain the advanced clip within the interior of the distal portion of the device. As the first pushrod 58 is once again advanced forward, it engages the clip 28 in the staging area with a force which overcomes the restraining force of the leaf spring, thereby pushing the forward-most clip 28 out toward the vessel to be ligated. The next clip in sequence is then in a position to be advanced into the staging area and the process is repeated.

Figure 27:
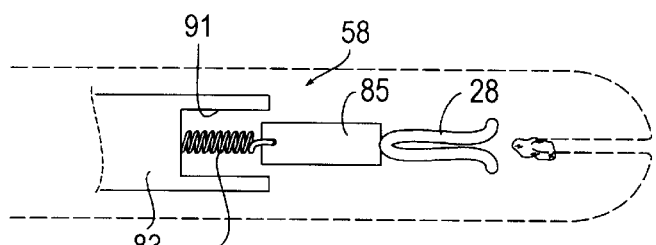
FIG. 27 is a partial cross-sectional view of an alternative preferred embodiment of the first pushrod.
Figure 28:
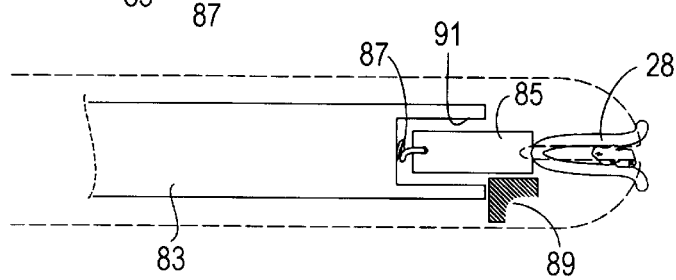
FIG. 28 is a partial cross-sectional view of the pushrod shown in FIG. 27 moved distally.
Figure 29:
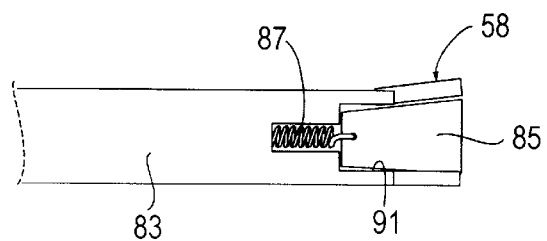
FIG. 29 is a partial cross-sectional view of an alternative embodiment of the pushrod shown in FIG. 28.

Additionally, as shown in FIGS. 27 and 28, in one preferred embodiment the first pushrod 58 is an assembly embodying a proximal portion 83, an actuator piston or distal portion 85, a spring 87 interspaced between the proximal portion and distal portion, and a stop 89. Proximal portion 83 includes a recess 91 configured in its terminal end within which the spring 87 is attached at one end and which is adapted to receive distal portion 85, to which the second end of the spring is attached. Such a pushrod has the advantage of guaranteeing that the vessel is located completely inside the clip 28 as well as controlling the force, by selecting springs with desired forces, which advances the clip 28 over the vessel. In operation, the pushrod assembly is advanced distally until the proximal portion 85 engages the stop. At this point, the clip has been advanced over the vessel. Where the vessel being ligated is very small in diameter so that the force to apply a clip over it is relatively small (ie., less than the force supplied by the spring), then the spring will advance the second portion of the pushrod and the clip further forward over the vessel. As shown in FIG. 29, the recess formed in the proximal portion of the pushrod can have a stepped configuration so that the spring does not have to be compressed to a solid height.

Furthermore, additional means for feeding a clip 28 may include electric motors or hydraulic pumps. The staging and loading of the clips may also be performed manually by devices attached to the actuating assembly 20 or elongated shaft 22. With such a manual means the clips could be loaded individually, by placing the clip into position to be advanced.

Figure 4:
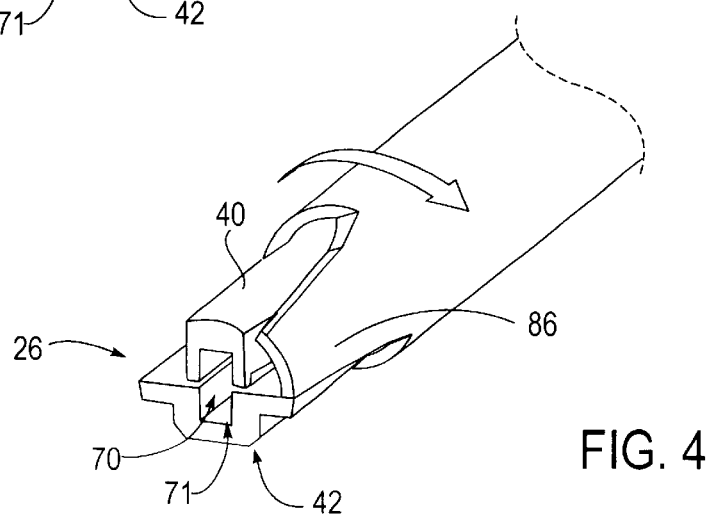
FIG. 4 is a perspective view depicting the manipulating assembly of FIG. 3 with the cutting member extended and rotated.

This invention may also be configured to cut the grasped body vessel 50, using an improved cutter. FIGS. 2 through 4 illustrate, by way of example, the features associated with this improvement. While the body vessel is grasped and crimped by the jaw 26, a cutting member 86 having at least one cutting edge 88 (as shown in FIGS. 30–33) may be advanced over the jaw and body vessel if it is not already there (See FIG. 34–36 which shows the rotating cutter 86 configured on the fixed jaw). The cutting member may then be rotated in either direction generally about the axis of the elongated shaft. As the cutting member is rotated one of the sharpened edges will cross the body vessel and cut it.

Figure 37:
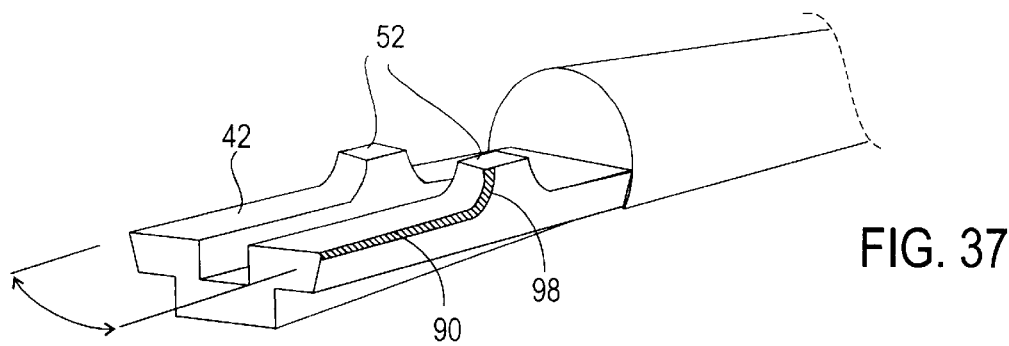
FIG. 37 is a perspective view depicting the fixed jaw member embodying features of the invention.

In the embodiment illustrated the cutting member 86 is a distal extension on the elongated shaft 22. The cutting member has cutting edges 88 along both sides. The fixed jaw member 42 has complementary cutting edges 90 (as shown in FIG. 37) along its sides, so that when the elongated shaft and cutting member are rotated the cutting edges of the cutting member and fixed jaw member cross each other in a scissoring action. Significantly, bi-directional cutting eliminates the need to rotate the distal end of the device to an appropriate position.

Figure 30:
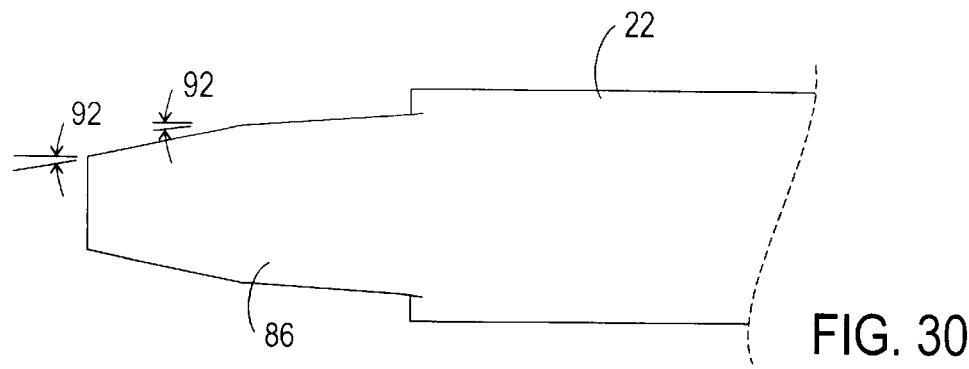
FIG. 30 is an elevational view depicting a first embodiment of the cutting member.
Figure 31:
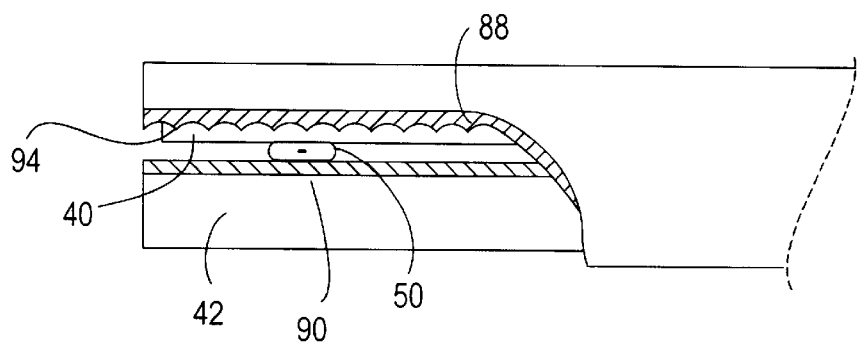
FIG. 31 is a side view depicting a second embodiment of the cutting member.
Figure 32:
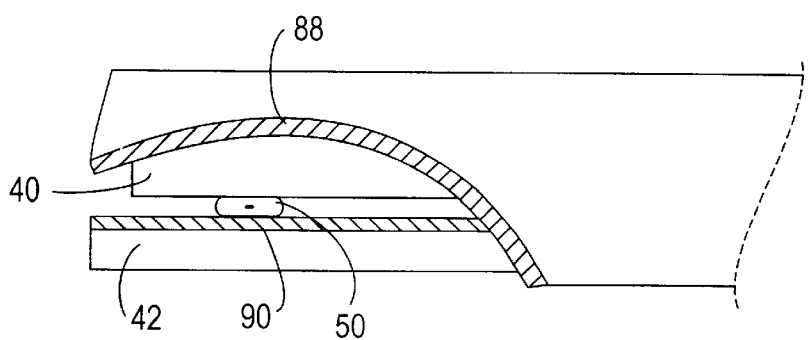
FIG. 32 is a side view depicting a third embodiment of the cutting member.
Figure 33:
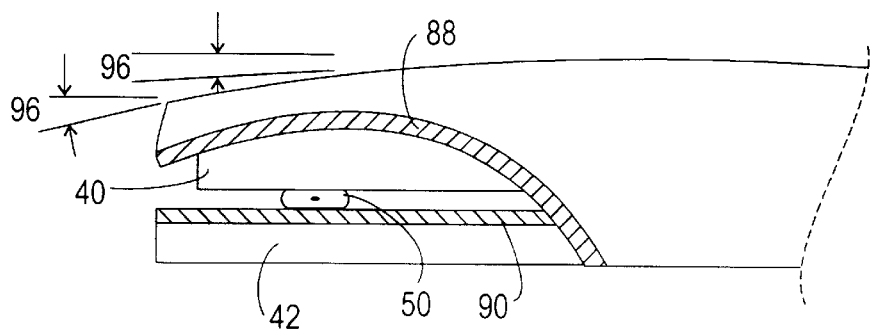
FIG. 33 is a side view depicting a fourth embodiment of the cutting member.

FIGS. 30–33 illustrate several possible configurations of the cutting member 86 and cutting edges 88. In one embodiment, as shown in FIG. 30, the cutting member and cutting edge have at least one angular bevel 92 which further narrows the extension near the distal tip. This improvement varies the angle of the cut during the cutting stroke. Another embodiment, as shown in FIG. 31, has serrations 94 in the cutting edges which increase the cutting efficiency and maintains the sharpness of the cutting edges. Another embodiment, as shown in FIG. 32, the cutting extension and cutting edges have the shape of an arc enclosing the area grasped by the jaw 26. This improvement captures the body vessel 50 to be cut as the arc-shaped cutting edge of the cutting member sweeps across the complementary cutting edges 90. Another embodiment, as shown in FIG. 33, the cutting member has at least one angular inward slant 96, which brings the distal tip of the cutting member closer to the cutting surface. This improvement increases the cutting force near the distal tip of the cutting member due to increased compression between the cutting edge and the complementary cutting edge as the cutting member is forced to bend against the slant.

Figure 38:
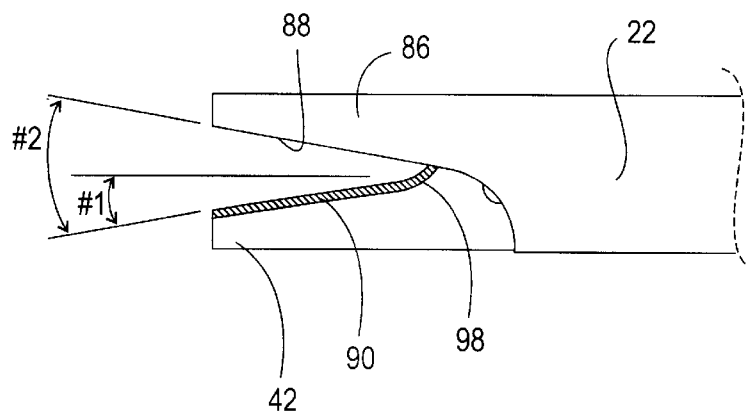
FIG. 38 is a perspective view depicting another preferred embodiment of the jaw members.

The fixed jaw member 42 can also be modified to increase cutting efficiency. The fixed jaw member can increase in width near the distal tip as illustrated in FIG. 37. This has a similar effect as slanting the cutting member 86 inward near the distal tip shown in FIG. 33. The compression is increased between the cutting edge 88 and the complementary edge 90 as the extension is forced to bend away from the increased width of the fixed jaw member. The ramps 52 near the proximal end of the fixed jaw member may also be edged to provide a lead-in edge 98 to prevent the edges from binding each other when cutting action is initiated. The edge on the cutting member may similarly have a lead-in edge 198 (FIG. 34) to replace or compliment the ramps 52. Another modification to jaw geometry 42 that can increase cutter scissoring action is illustrated in FIG. 38. This modification can be made while maintaining jaw geometry similar to FIG. 37 or having a straight profile. Angle #2 in FIG. 38 is increased by canting the surface, on top of and adjacent to edge 90, an angle #1.

The increased angle #2 is an increased angle between cutting edges 90 and 98 and can improve cutter scissoring action.

Figure 34:
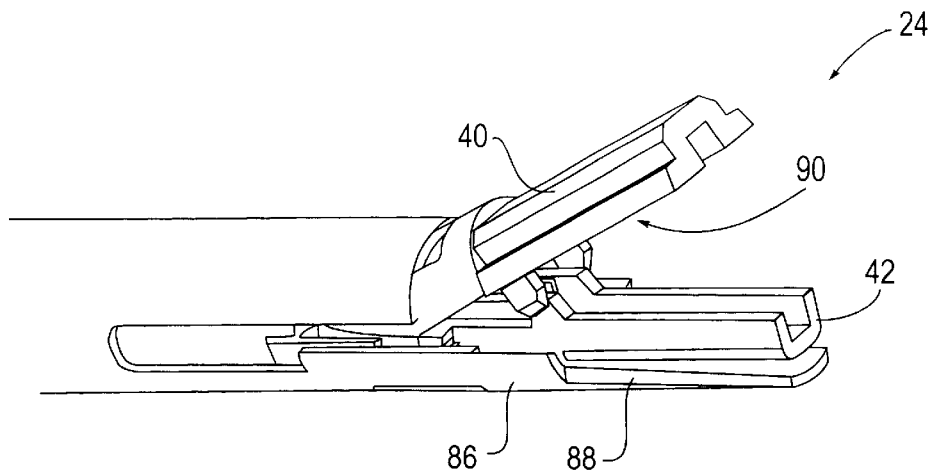
FIG. 34 is a perspective view depicting an alternative embodiment of the manipulating and cutting assembly with the jaws in an open position.
Figure 35:
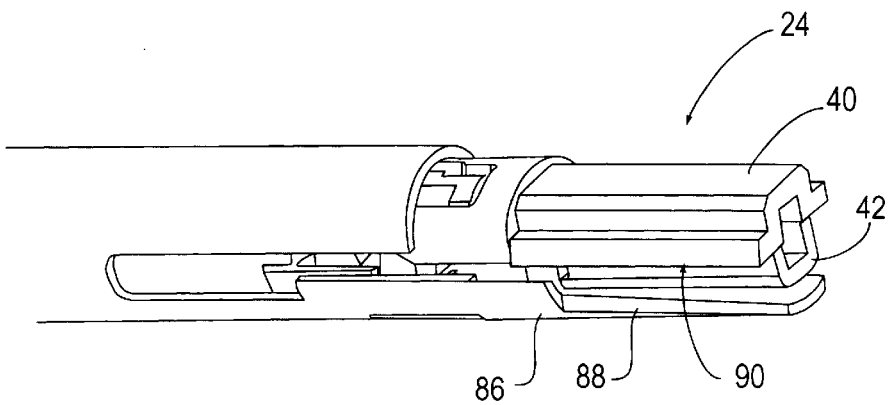
FIG. 35 is a perspective view of the device shown in FIG. 34, showing the jaws in a closed position.
Figure 36:
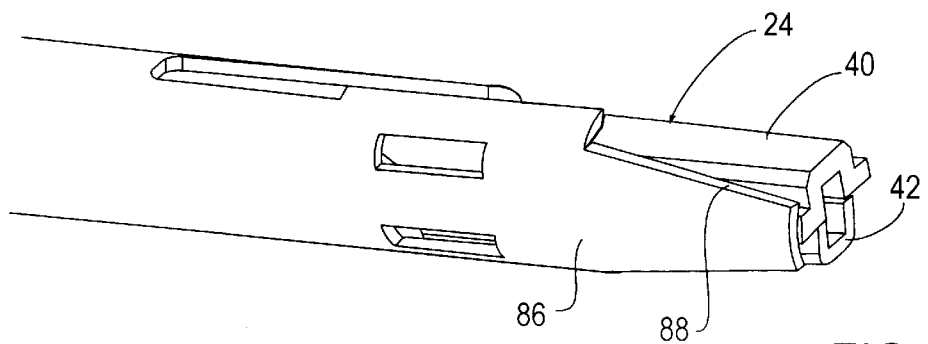
FIG. 36 is a perspective view of the device shown in FIG. 35, showing the cutter being rotated.

Most examples have shown the cutting member 86 cutting on the complementary edge 90 on the fixed jaw, but the cutting member 86 can cut on the complimentary edge 90 on the hinged 25 jaw also (See FIG. 34–36). This is a more preferred method because no distal/proximal translation is required for 86 to stay clear of the hinged jaw in the open position. Rotating 86 is the only movement required for cutting.

Figure 39:
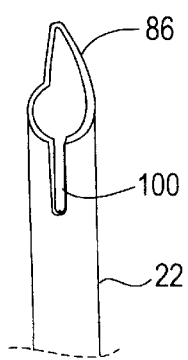
FIG. 39 is a perspective view depicting a first embodiment of slots in the cutting member and elongated shaft.
Figure 40:
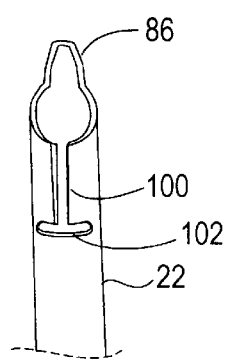
FIG. 40 is a perspective view depicting a second embodiment of slots in the cutting member and elongated shaft.
Figure 41:
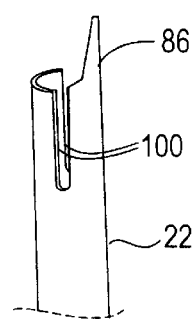
FIG. 41 is a perspective view depicting a third embodiment of slots in the cutting member and elongated shaft.

As illustrated in FIG. 39, there are modifications to the elongated shaft 22 which improve the cutting efficiency. Slots in the elongated shaft may be used to increase the flexibility of the elongated shaft, reducing the tendency of the cutting member 86 to bind on the complementary cutting edge 90. FIG. 39 depicts a single longitudinal slot 100 in the elongated shaft opposite the cutting member. The slot extends from the distal end of the elongated shaft a distance sufficient to provide the desired flexibility. A similar longitudinal slot 100 in combination with a radial slot 102 is depicted in FIG. 40. The radial slot extends radially from both sides of the longitudinal slot a distance sufficient to provide the desired flexibility. Another embodiment, as shown in FIG. 41, has a pair of longitudinal slots 100 on opposite sides of the elongated shaft. Both slots are at the sides of the cutting extension, and extend a sufficient distance to provide the desired flexibility.

The cutting member 86 has cutting edges 88 on both sides as well as the fixed or hinged jaw member 42 or 40 having complementary edges 90 on both sides so that rotation of the cutting member in either direction will produce a cutting action. In the illustrated embodiment the cutting member is rotated by rotating the entire elongated shaft 22. The elongated shaft is rotated using the cutting knob 38 or other mechanical actuating means (See FIG. 5, button 108) located within the actuating assembly 20.

As depicted in FIG. 2, while the jaw 26 is in the open position 54 the elongated shaft 22 and cutting member 86 are positioned proximal to the jaw. When the jaw 26 is in the closed position, the elongated shaft can be advanced distally so that the cutting member extends over the jaw and any body vessel 50 grasped by the jaw, provided it is not already so configured. The cutting member can then be rotated in either direction depending on which side the cut is desired.

The elongated shaft 22, which is integral with the cutting member 86, extends proximally to the actuating assembly 20 where it is fixedly attached to a cutting knob 38 which extends generally perpendicular to the shaft. The cutter knob is adapted to be manually controlled, and extends out of the barrel 34. The knob is seated within two slots in the barrel. A longitudinal slot 104 extends distally through the barrel a length which is sufficient to advance and retract the cutting member 86 from its fully extended position to its fully retracted position, approximately a half inch. A radial slot 106 extends in both directions from the distal end of the horizontal slot. The slot extends a sufficient distance around the barrel to rotate the cutting member through a complete cut along the complementary cutting edge 90, approximately 90 degrees around the barrel in both directions. The slots are wide enough to accept the cutting knob.

The embodiments of these features may vary without affecting the operability of the invention. The cutting member 86 has been illustrated as integral with the elongated shaft 22. The cutting member may also be a separate structure located outside or within the elongated shaft. The advancing and rotating of the cutting member may be accomplished with similar mechanical and mechanical assisted means. Furthermore, the complementary cutting edges 90 may be on separate structure instead of on the fixed jaw member 42 or on the hinged jaw 40.

The improvements of this instrument allow for an improved process of ligating and possibly cutting a body vessel. Using the invention with the features identified, an operator grasps the handle 32 of the actuating assembly 20 and percutaneously inserts the manipulating assembly 24 and elongated shaft 22 into the patient. The manipulating assembly is then advanced to the body vessel 50 to be treated.

The body vessel 50 is positioned between the hinged jaw member 40 and the fixed jaw member 42 while the jaw 26 is in the open position 54, and the cutting member 86 is retracted. By squeezing the trigger 36 a certain distance the jaw is actuated into the closed position 56 grasping and crimping the body vessel 50.

With the body vessel 50 grasped and crimped within the jaw 26 the operator may then continue with the procedure either by ligating the body vessel with an improved clip 28 or by cutting the body vessel. The operator may also choose to combine ligating and cutting the body vessel in different orders.

To ligate the vessel the operator may, for example, further squeeze the trigger 36 so that an improved clip 28 is advanced over the body vessel 50. With the body vessel ligated the operator releases the trigger to a certain position which loads another clip to be advanced. The operator may then choose to cut the vessel or release the jaw and remove the instrument from the body vessel.

To cut the vessel, either before, after, or without ligating the vessel, the operator may, for example, distally advance the cutting knob 38, which distally advances the cutting member 86 over the jaw 26 and the body vessel 50. The operator may then choose to cut the body vessel on either side, or both sides, of the jaw. To cut the body vessel on any particular side of the jaw the operator rotates the cutting knob through the radial slot 106 on the corresponding side of the barrel 34. With the body vessel cut the operator returns the cutting member to the retracted position by rotating the cutting knob back to the upright position and retracting it proximally within the horizontal slot 106 in the barrel. The operator may then choose to cut the vessel on the opposite side of the jaw, ligate the vessel with an improved clip 28, or release the vessel. Again, the preferred embodiment has the cutting member 86 rotating over hinged jaw 40 to produce cutting action. No proximal/distal translation of 86 is required for this embodiment. Rotating the cutting member 86 is all that is required to cut the vessel in this preferred embodiment.

The operator may release the body vessel 50, with or without cutting the member by, for example, releasing the trigger 36 which actuates the jaw 26 into the open position 54. The operator may then either retract the instrument from the patient or proceed to treat other portions of the same or different body vessels. With this instrument the operator may cut an indefinite number of body vessels within an individual procedure. Furthermore, since the instrument contains a plurality of improved clips 74 which are automatically loaded to ligate a vessel once another clip has been used, the device may be used to ligate several vessels within a single procedure.

The operator may choose to use this instrument in harvesting a body vessel 50. Body vessels are harvested for many reasons, including transplant and biopsy procedures. To harvest a body vessel the operator first frees the selected body vessel by using this instrument to cut and ligate the body vessel in multiple locations. Once the body vessel has been freed from its connections to the body the operator grasps the vessel by squeezing the trigger 36 and actuating the jaw 26 into the closed position 56 over the body vessel. Once the body vessel is firmly grasped the operator withdraws the instrument and the vessel from the body. The operator then released the trigger and actuates the jaw into the open position 54, releasing the body vessel. Such a vessel is then available for the procedures required.

As can be seen, the improvements of this method are the efficiency with which body vessels can be ligated and cut, as well as the flexibility the improved invention gives the operator in deciding how to continue in the procedure. The efficiency in ligating body vessels is provided by the improved grasping means of the jaw 26 and the improved ligating means of the improved clip 28. The efficiency in cutting body vessels is provided by the improved cutting means of the rotating cutting member 86.

The instrument of the invention may be made from various materials such as metals, preferably stainless steel, plastics, preferably a polycarbonate or polyetherimide resin, or the like. The instrument may also be made from a combination of materials. Usually if the instrument, or portions thereof, are made from stainless steel those portions will be reusable after sterilizing. Those portions made from plastic materials will be disposable or reusable. The instrument may be designed to accept a replaceable storage tube of clips and this may be accomplished with a reusable storage tube or a disposable one.

The improved clip 28 of the invention may be made from various known metals, for example, stainless steel, titanium, tantalum, super-elastic memory metals or the like, or possibly from plastic materials that have sufficient resilience, such as poly olefins, glycolide-lactide polymers or similar plastics.

While the present invention has been described in terms of a simple mechanical device, there are multiple means which will achieve the same purposes. An electric device with the same basic design may employ electric motors and other devices to perform the functions of the invention, such as, actuating the jaw 26, advancing the clips 28, rotating the cutting member 86 and inserting and withdrawing the instrument itself. One possible advantage of such an electric embodiment would be the addition of computerized or electronic control of the functions. The same functions could also be accomplished using hydraulic or pneumatic means. With these embodiments the instrument would employ pressurized fluids behind pistons to actuate the manipulating assembly 24. Possible advantages of these embodiments would be greater forces applied and more precision accomplished in the procedure.

While the present invention has been described in terms of specific preferred embodiments it will be readily apparent to those skilled in the art that various modifications and alterations may be made without departing from the scope of the invention. Although this device has been presented as an endoscopic instrument it may also be used, with or without adaptation, in other types of surgical procedures. This device has been described in terms of performing procedures on body vessels, such as veins or arteries, however, those skilled in the art will recognize that this device can be used on various body tissues.

What is claimed is:

1. A system for performing a surgical technique, comprising:

an actuating assembly at the proximal end of an elongated shaft;

a manipulating assembly at the distal end of said elongated shaft, said manipulating assembly including jaw members, said jaw members having an open and a closed configuration;

a cutting device at the distal end of said elongated shaft said cutting device capable of rotating about said jaw members when said jaw members are in said closed position; and said actuating assembly operatively connected to said manipulating assembly and said cutting device.

2. The system of claim 1, said actuating assembly further comprising a trigger operatively connected to said manipulating assembly such that actuation of said trigger causes the jaw members to assume open or closed positions.

3. The system of claim 2, further comprising a first pushrod configured longitudinally within said tubular shaft, said first pushrod operatively associated with said trigger such that actuation of said trigger causes said first pushrod to travel longitudinally with respect to said manipulating assembly.

4. The system of claim 3, further comprising a second pushrod configured longitudinally within said tubular shaft and positioned adjacent said first pushrod, said second pushrod operatively associated with said trigger such that actuation of said trigger causes said second pushrod to travel longitudinally with respect to said manipulating assembly.

5. The system of claim 4, further comprising a side ram, said side ram being configured within said tubular shaft and operating to direct at least one clip into a staging area which is in alignment with said second pushrod.

6. The system of claim 5, wherein said side ram is spring loaded.

7. The system of claim 5, further comprising a leaf spring, said leaf spring operating to contain at least one clip within said staging area.

8. The system of claim 5, said second pushrod further comprising a device for controllably further advancing a clip against minimal resistive forces.

9. The system of claim 1, further comprising a plurality of clips housed within said elongate shaft.

10. The system of claim 9, further comprising a clip advancing assembly that facilitates advancing at least one clip between said jaw members.

11. The system of claim 1, wherein one said jaw member pivots with respect to the other said jaw member.

12. The system of claim 1, wherein at least one said jaw member includes a cutting edge which cooperates with said cutting device.

13. The system of claim 1, said actuating assembly further comprising a knob operatively connected to said cutting device such that actuation of said knob causes the cutting device to rotate.

14. A method for ligating and cutting tissue using a device including a manipulating assembly, a rotatable cutter device, a plurality of clips and structure for advancing the clips over tissue, the method comprising:

capturing tissue with the manipulating assembly;

advancing at least one clip over the tissue to be ligated; and rotating said cutter device to thereby cut the tissue.

15. The method of claim 14 wherein each of said clips includes an open end having diverging lip members and wherein said advancing includes spreading said lip members.

16. A system for performing a surgical technique, comprising:

an actuating assembly;

an elongated shaft extending distally away from said actuating assembly, said shaft having a proximal end and a distal end;

a manipulating assembly at said distal end of said shaft, said manipulating assembly including jaw members, one said jaw member pivotable with respect to the other said jaw member, said jaw members having an open and a closed configuration; and a cutting device, said cutting device capable of rotating about said jaw members when said jaw members are in said closed position, wherein said actuating assembly is operatively connected to said manipulating assembly.

17. The system of claim 16, said actuating assembly further comprising a trigger operatively connected to said manipulating assembly such that actuation of said trigger causes the jaw members to assume open or closed positions.

18. The system of claim 17, further comprising a first pushrod configured longitudinally within said tubular shaft, said first pushrod operatively associated with said trigger such that actuation of said trigger causes said first pushrod to travel longitudinally with respect to said manipulating assembly.

19. The system of claim 18, further comprising a second pushrod configured longitudinally within said tubular shaft and positioned adjacent said first pushrod, said second pushrod operatively associated with said trigger such that actuation of said trigger causes said second pushrod to travel longitudinally with respect to said manipulating assembly.

20. The system of claim 19, further comprising a side ram, said side ram being configured within said tubular shaft and operating to direct at least one clip into a staging area which is in alignment with said second pushrod.

21. The system of claim 20, wherein said side ram is spring loaded.

22. The system of claim 20, further comprising a leaf spring, said leaf spring operating to contain at least one clip within said staging area.

23. The system of claim 20, said second pushrod further comprising a device for controllably further advancing a clip against minimal resistive forces.

24. The system of claim 16, further comprising a plurality of clips housed within said elongate shaft.

25. The system of claim 24, further comprising a clip advancing assembly that facilitates advancing at least one clip between said jaw members.

26. The system of claim 16, wherein at least one said jaw member includes a cutting edge which cooperates with said cutting device.

27. The system of claim 16, said actuating assembly further comprising a knob operatively connected to said cutting device such that actuation of said knob causes said cutting device to rotate.

28. A system for performing a surgical technique, comprising:

an actuating assembly including a knob;

an elongated shaft extending distally from said actuating assembly, said shaft having a proximal end and a distal end;

a manipulating assembly at said distal end of said shaft, said manipulating assembly including jaw members, said jaw members having an open and a closed configuration; and a cutting device at said distal end of said shaft, said cutting device capable of rotating about said jaw members when said jaw members are in said closed position, wherein said actuating assembly is operatively connected to said manipulating assembly and said cutting device, and said knob is operatively connected to said cutting device such that actuation of said knob causes the said cutting device to rotate.

29. The system of claim 28, said actuating assembly further comprising a trigger operatively connected to said manipulating assembly such that actuation of said trigger causes the jaw members to assume open or closed positions.

30. The system of claim 29, further comprising a first pushrod configured longitudinally within said tubular shaft, said first pushrod operatively associated with said trigger such that actuation of said trigger causes said first pushrod to travel longitudinally with respect to said manipulating assembly.

31. The system of claim 30, further comprising a second pushrod configured longitudinally within said tubular shaft and positioned adjacent said first pushrod, said second pushrod operatively associated with said trigger such that actuation of said trigger causes said second pushrod to travel longitudinally with respect to said manipulating assembly.

32. The system of claim 31, further comprising a side ram, said side ram being configured within said tubular shaft and operating to direct at least one clip into a staging area which is in alignment with said second pushrod.

33. The system of claim 32, wherein said side ram is spring loaded.

34. The system of claim 32, further comprising a leaf spring, said leaf spring operating to contain at least one clip within said staging area.

35. The system of claim 32, said second pushrod further comprising a device for controllably further advancing a clip against minimal resistive forces.

36. The system of claim 28, further comprising a plurality of clips housed within said elongate shaft.

37. The system of claim 36, further comprising a clip advancing assembly that facilitates advancing at least one clip between said jaw members.

38. The system of claim 28, wherein one said jaw member pivots with respect to the other said jaw member.

39. The system of claim 28, wherein at least one said jaw member includes a cutting edge which cooperates with said cutting device.

40. A system for performing a surgical technique, comprising:

an actuating assembly including a trigger;

an elongated shaft extending distally away from said actuating assembly, said shaft having a proximal end and a distal end;

a manipulating assembly at said distal end of said shaft, said manipulating assembly including jaw members, said jaw members having an open and a closed configuration, wherein said trigger is operatively connected to said manipulating assembly such that actuation of said trigger causes the jaw members to assume open or closed positions;

a cutting device at said distal end of said shaft, said cutting device capable of rotating about said jaw members when said jaw members are in said closed position, wherein said actuating assembly is operatively connected to said manipulating assembly;

a first pushrod configured longitudinally within said tubular shaft, said first pushrod operatively associated with said trigger such that actuation of said trigger causes said first pushrod to travel longitudinally with respect to said manipulating assembly; and a second pushrod configured longitudinally within said tubular shaft and positioned adjacent said first pushrod, said second pushrod operatively associated with said trigger such that actuation of said trigger causes said second pushrod to travel longitudinally with respect to said manipulating assembly.

41. The system of claim 40, further comprising a side ram, said side ram being configured within said tubular shaft and operating to direct at least one clip into a staging area which is in alignment with said second pushrod.

42. The system of claim 41, wherein said side ram is spring loaded.

43. The system of claim 41, further comprising a leaf spring, said leaf spring operating to contain at least one clip within said staging area.

44. The system of claim 41, said second pushrod further comprising a device for controllably further advancing a clip against minimal resistive forces.

45. The system of claim 40, further comprising a plurality of clips housed within said elongate shaft.

46. The system of claim 45, further comprising a clip advancing assembly that facilitates advancing at least one clip between said jaw members.

47. The system of claim 40, said actuating assembly further comprising a knob operatively connected to said cutting device whereby actuation of said knob causes said cutting device to rotate.

48. The system of claim 40, wherein one said jaw member pivots with respect to the other said jaw member.

49. The system of claim 40, wherein at least one said jaw member includes a cutting edge which cooperates with said cutting device.

* * * * *

UNITED STATES PATENT AND TRADEMARK OFFICE
CERTIFICATE OF CORRECTION

PATENT NO.   : 6,241,740 B1              Page 1 of 1
DATED        : June 5, 2001
INVENTOR(S)  : Davis et al.

It is certified that error appears in the above-identified patent and that said Letters Patent is hereby corrected as shown below:

<u>Title page,</u>
Item [56], References Cited, FOREIGN PATENT DOCUMENTS, please delete reference number "5692230A1" and insert -- 569223-A1 --.
OTHER PUBLICATIONS, please delete "Laparoscopic Sterilization with Spring Clips" and insert -- *Laparoscopic Sterilization with Spring Clips* --.

Signed and Sealed this

Seventh Day of October, 2003

JAMES E. ROGAN
*Director of the United States Patent and Trademark Office*